United States Patent [19]

Milosevic et al.

[11] Patent Number: 4,853,542
[45] Date of Patent: Aug. 1, 1989

[54] COLLECTING HEMISPHERICAL ATTACHMENT FOR SPECTROPHOTOMETRY

[75] Inventors: Milan Milosevic, Fishkill, N.Y.; Nicolas J. Harrick, Croton Dam Rd., Ossining, N.Y. 10562

[73] Assignee: Nicolas J. Harrick, Ossining, N.Y.

[21] Appl. No.: 59,323

[22] Filed: Jun. 8, 1987

[51] Int. Cl.[4] .............................................. G01J 3/44
[52] U.S. Cl. ..................................... 250/353; 250/339; 250/228; 250/372; 356/446; 356/239
[58] Field of Search ............... 250/353, 341, 372, 228, 250/339; 356/446, 236

[56] References Cited

U.S. PATENT DOCUMENTS

| | | | |
|---|---|---|---|
| 3,349,665 | 10/1967 | Grosheim et al. | 356/236 |
| 4,158,772 | 6/1979 | Reedy | 250/341 |
| 4,378,159 | 3/1983 | Galbraith | 356/236 |
| 4,548,506 | 10/1985 | Elson | 356/446 |
| 4,645,340 | 2/1987 | Graham et al. | 356/301 |
| 4,661,706 | 4/1987 | Messerschmidt et al. | 250/353 |
| 4,724,345 | 12/1987 | Schrader | 356/301 |

Primary Examiner—Carolyn E. Fields
Assistant Examiner—John A. Miller

[57] ABSTRACT

An attachment or accessory for performing diffuse reflectance spectroscopy on a conventional UV-VIS-IR spectrophotometer. The attachment includes a removable body having a hemispherical mirrored interior surface positioned over the sample, and containing windows for entrance and exit of radiation. Multiple sampling of the same sample area enhances the quality of the spectrophotometer output.

9 Claims, 4 Drawing Sheets

COLLECTING HEMISPHERICAL ATTACHMENT FOR SPECTROPHOTOMETRY

FIELD OF THE INVENTION

This invention relates to spectrophotometry, and in particular to an attachment usable with conventional spectrophotometers in the ultraviolet (UV), visible (VIS) and infrared (IR) spectral ranges. The attachment is especially suited for use with accessories in diffuse reflectance spectrophotometry.

BACKGROUND OF THE INVENTION

Diffuse reflectance spectroscopy is a well known technique especially useful for analyzing samples of materials that are difficult to analyze by classical techniques. Powders and rough surface solids are examples of samples that can be well handled by diffuse reflectance spectroscopy. Various optical geometries for this purpose have been described in the literature. See, for instance, the article by Brimmer, Griffiths and Harrick on pages 258-265 of Vol. 40, No. 2, 1986 of Applied Spectroscopy, and the references cited therein. The aforementioned article is herein incorporated by reference. As described in that article, a number of diffuse reflectance accessories have been developed commercially to fit into the sample compartments of most of the Fourier Transform Infrared (FT-IR) spectrometers as well as the older dispersive-type spectrometers. A typical accessory comprises a base or support plate which can be seated in the sampling compartment of the spectrometer. The base supports one or more plane mirrors for receiving the incoming beam from the spectrometer and redirecting it to a first focussing mirror which focusses the beam at a selected angle onto the sample surface. Typically, the sample is a powder pressed into a recess on a post also mounted on the base. The diffuse reflections from the sample are collected by a second focussing mirror which passes the reflected beam to one or more plane mirrors which in turn redirect the beam back into the spectrometer so it can impinge on the usual detector which converts the beam into an electrical signal. The electrical signal is processed in the standard fashion to produce, typically, a graph which relates the signal intensity to the wavelength of the incident beam. The diffuse reflection is a function, among other things, of the sample absorptivity and thus the output is typically plotted as %-transmittance as a function of wavelength or more commonly wavenumbers. One popular diffuse reflection accessory is manufactured by Harrick Scientific Corp. and is widely known as the "Praying Mantis" Model due to the configuration of the focussing mirrors which are large ellipsoid mirrors positioned over the sampling post.

Diffusely reflected radiation is spread out in the half of the full solid angle measured from the sample surface. Though the second ellipsoidal mirror is a large segment, a considerable amount of diffusely reflected radiation from the sample escapes uncollected. This reduces the quality of the output. In addition, for poorly reflecting samples, the signal-to-noise (S/N) ratio is poor.

SUMMARY OF THE INVENTION

One object of the invention is a spectrometer providing improved output.

A further object of the invention is an accessory for diffuse reflectance spectrometry providing an output signal that exhibits a higher S/N ratio, or a higher optical throughput, or a higher spectral contrast, or several of the latter.

Another object of the invention is an attachment for existing diffuse reflectance accessories for increasing the collection of diffusely reflected radiation.

These and other objects and advantages of the invention are achieved, briefly speaking, with a hemispherical hollow optical element having a mirrored interior surface. The hemispherical element is positioned over the sample post such that the focus of the incident radiation on the sampling surface substantially coincides with the center of curvature of the inside surface of the hemispherical element. Windows in the form of openings are provided in the surface of the hemispherical element, to allow the incident beam to impinge on the sample surface at the desired angle of incidence, and to allow the diffusely reflected beam to exit. The improved performance results from multiple reflections of the diffuse and specular radiation back onto the sample and enhanced collection of the diffusely reflected radiation.

BRIEF DESCRIPTION OF THE DRAWINGS

The invention will now be explained in greater detail with reference to the accompanying drawings, wherein.

DETAILED DESCRIPTION OF A PREFERRED EMBODIMENT

Figure 1:
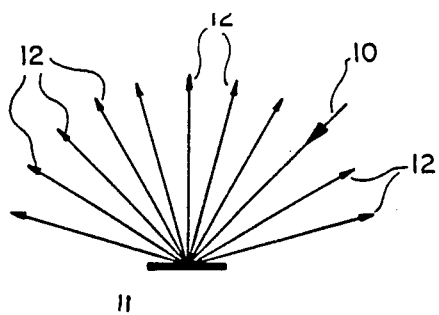
FIG. 1 is a schematic drawing illustrating diffuse reflection from a sample surface.
Figure 2:
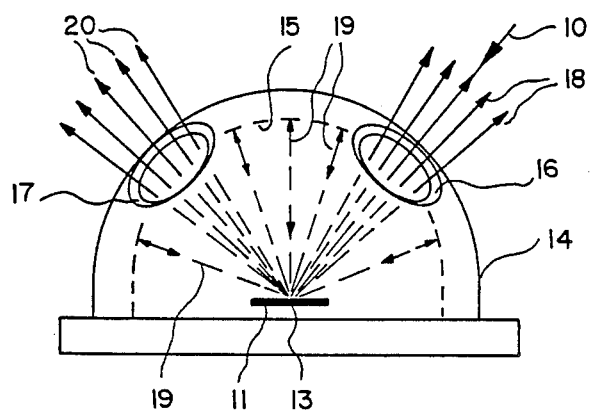
FIGS. 2 and 3 are respectively side and top schematic views illustrating typical radiation ray paths with one embodiment of the invention.
Figure 3:
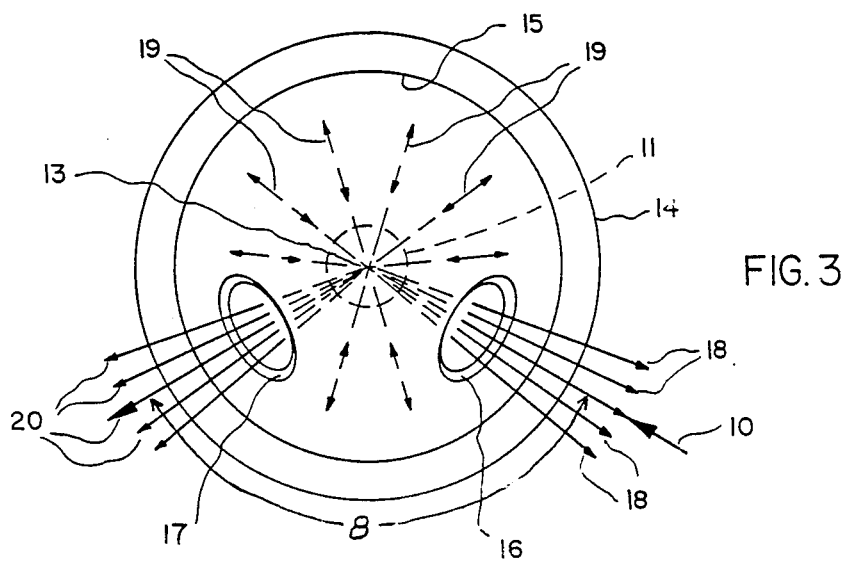

FIG. 1 shows an incident radiation beam 10 inpinging on the surface of a sample 11. A beam which penetrates into the specimen will typically undergo refraction, scattering and absorption. The radiation 12 emerging from the sample will be diffusely reflected and will spread out in the half of the full solid angle. One object of the invention is to collect as much as possible of this diffusely reflected radiation to increase the signal level of the measurement. In accordance with the invention, the sample 11 is enclosed by a hemispherical shell 14 having a highly reflective inside surface 15 and is provided with windows or openings 16, 17 to allow the incident radiation beam 10 to enter and impinge upon the sample surface and to allow that portion of the diffusely reflected radiation that can be collected by the external focussing mirror to exit from the enclosure. This is illustrated in FIGS. 2 and 3. As will be observed, some of the diffusely reflected radiation 18 is lost through the entrance window 16. Some of it 20 leaves through the exit window 17 and will get collected and detected. Most of the radiation 19, scattered over $2\pi$ steradians is intercepted by the hemisphere 14 and, in the preferred geometry, with the center of curvature of the hemisphere substantially coincident with the focus of the incident beam, the point designated 13, will be reimaged back to the same point 13 by the spherical mirror surface 15. Thus, otherwise uncollected radiation in the prior art constructions is captured by the hemispherical reflector 14, refocussed back onto the sampling area 11, and receives another chance to exit the hemisphere by way of the exiting window 17 and be collected by the external mirrors. Advantage is here taken of the fact that a spherical reflector refocusses all the radiation that comes from its center back to the same point.

Figure 5:
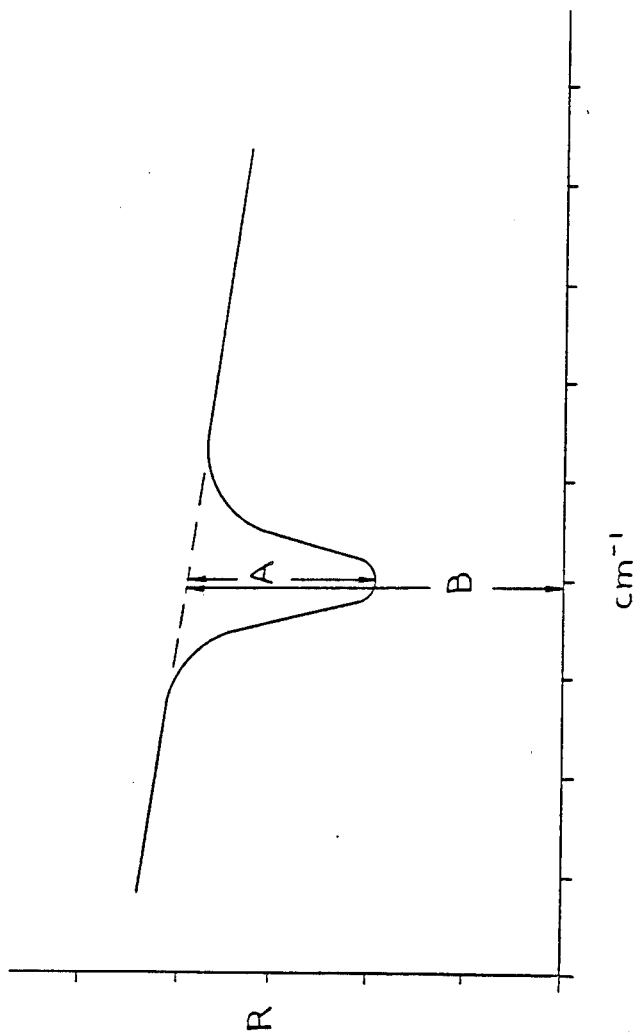
FIG. 5 is a graph to explain several characteristics discussed in the specification.

In the construction of the invention, not only does a considerably larger portion of the diffuse radiation reach the detector, but another, possibly even more important, effect is obtained. That is, the radiation has impinged a second time on essentially the same point 13 of the sample 11. Since the phenomenon continues, the same point of the sample gets multiplly sampled. It is important to note that the sampling area has not increased by this multiple sampling. The result is that the hemispherical attachment 14 will convert a standard diffuse reflectance accessory into a multiple unipoint sampling accessory. This not only increases the S/N ratio, but also, in general, the optical throughput and the spectral contrast. FIG. 5 illustrates these optical characteristics. The graph shown therein plots reflectance R as a function of wavenumber ($cm^{-1}$) for some arbitrary sample having one absorption peak as shown. By energy throughput is meant the height B of an extension of the curve (shown by the dashed line) at the peak, while with spectral contrast is meant the ratio A/B of the absorption to the height of the curve extension. In the invention, increases in optical throughput of roughly 50% have been obtained, while spectral contrast increases of roughly 100% have been achieved. It will be understood that in diffuse reflectance spectrometry, the ideal output radiation will be entirely diffuse radiation. The dome 14 can be viewed as a means for converting specular or partially specular radiation into diffuse radiation so that more of the beam radiation energy is concentrated into the diffuse radiation mode which contains the information of interest to the user.

Figure 4:
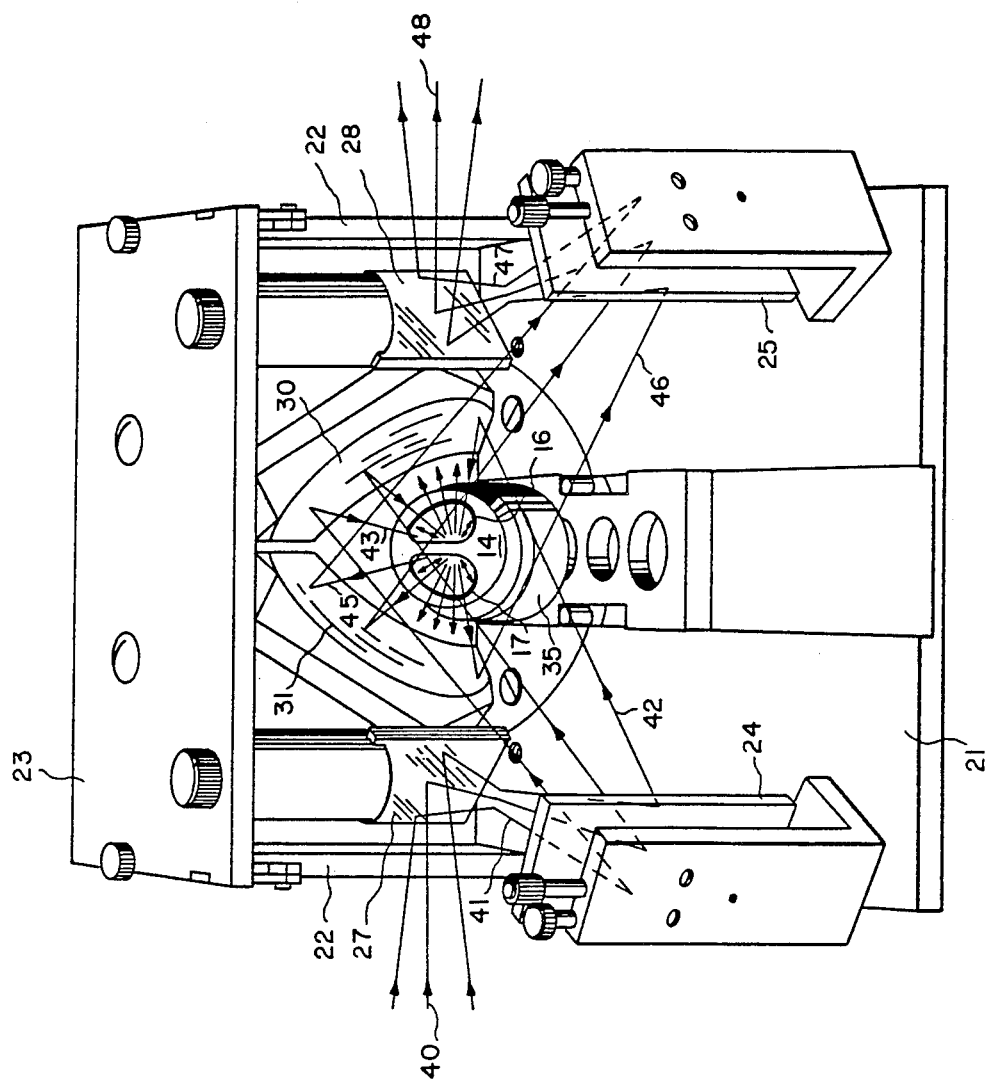
FIG. 4 is a view from the front showing one form of diffuse reflectance accessory of the invention using a hemispherical element similar to that illustrated in FIG. 2.

FIG. 4 is a front perspective view of the Praying Mantis accessory above described fitted with the attachment of the invention. It comprises a base plate or support 21 on which is mounted at the rear two upright plates 22 on which a top plate 23 is mounted. At the left front is mounted a first plane mirror 24 in a generally vertical position, which is adjustable, and a second plane mirror 25 is symmetrically positioned at the right front. A third plane mirror 27 is suspended from the top plate 23, also adjustable, and a fourth plane mirror 28 is symmetrically positioned at the opposite side. Two elliptical mirror segments 30, 31 are suspended from the top plate 23. In the center of the base plate 21 is mounted a sampling post (not visible), which is merely a cylindrical post with a recess in its top surface for receiving the sample to be analyzed. This corresponds to element 11 in FIGS. 1–3. A support ring 35 is also mounted on the base plate and on this support ring is seated the hemispherical attachment 14 illustrated in FIGS. 2 and 3. The geometry is chosen so that the center of curvature of inner reflecting surface 15 of the hemisphere 14 substantially coicides with the focus of the focussing ellipsoid 30 and collecting ellipsoid 31. The sample 11 is packed into the top of the sampling post. For this purpose, the dome 14 is removable to provide access to the sampling post. The accessory is then placed in the sampling compartment of the spectrometer, simply seated on its base plate 21.

In operation, the incident beam 40 from the spectrometer is intercepted by the third plane mirror 27, redirected 41 to the first plane mirror 24, from which it is redirected 42 to the first focussing ellipsoid mirror 30. From the latter, the incident beam 43 is directed through the entrance window 16 of the attachment 14 and is focussed onto a point at the sample surface. Diffuse reflectance occurs as shown in FIGS. 2 and 3, and as previously described, some exits by way of the exit window 17, and other rays are intercepted by the inside mirror 15 of the hemisphere 14 and refocussed back onto substantially the same point of the sample. The diffuse radiation 45 directed toward the exit window is collected by the second focussing ellipsoid mirror 31 from whence it follows a path symmetrical to the incident path, shown by numerals 46, 47 and 48, which places it back in the path the incident beam would have taken had the accessory not been present. In other words, the original focussing conditions are maintained. The beam 48 reenters the spectrometer and is there detected and the resultant signal or signals processed in the normal way.

Figure 6:
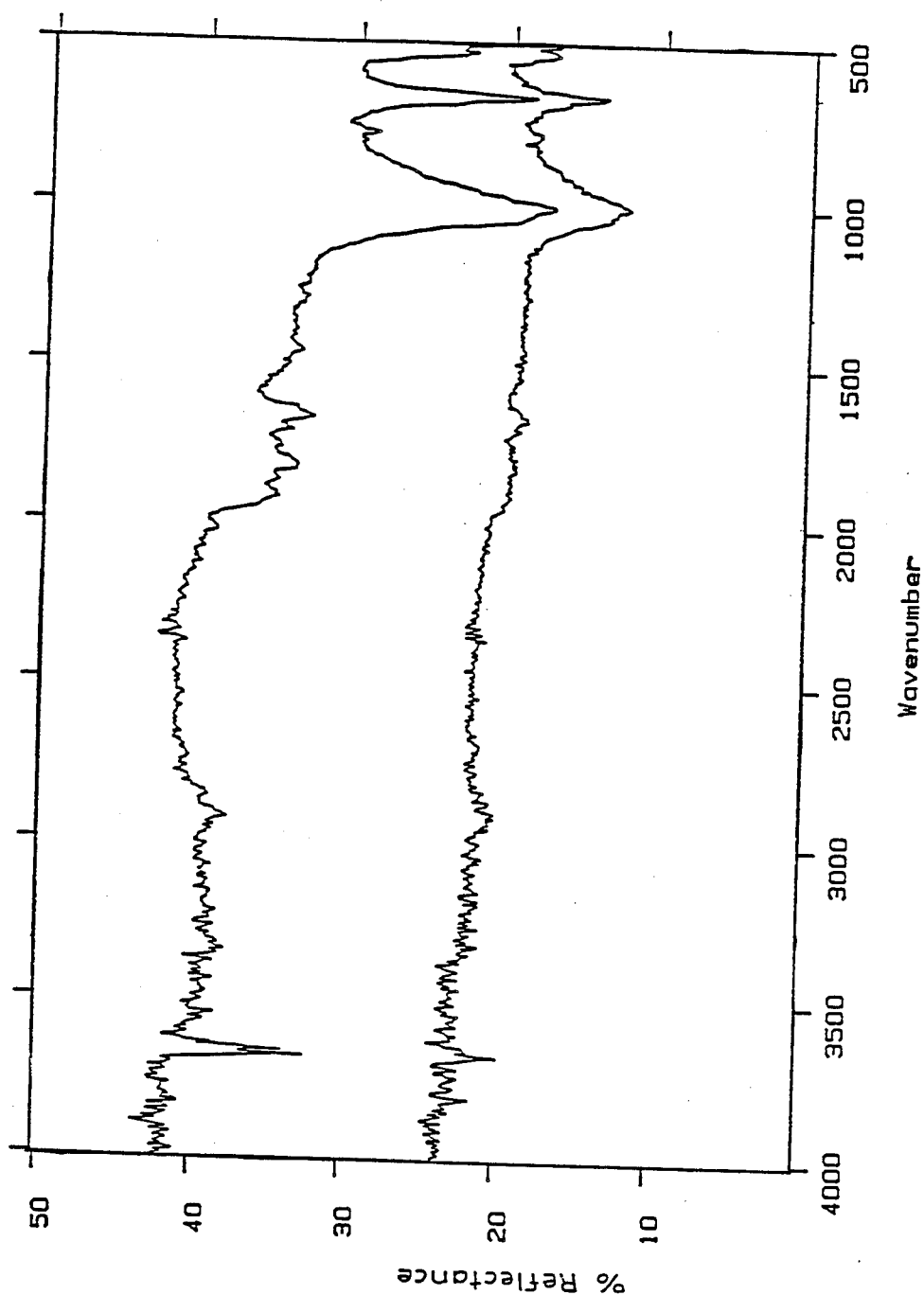
FIG. 6 is a graph containing two spectra of the same sample taken with a conventional FT-IR spectrometer with and without the attachment of the invention being present.

FIG. 6 illustrates some of the benefits obtainable with the invention. The apparatus illustrated in FIG. 4 was used to obtain the diffuse radiation spectrum of a sample of less than 0.5% talcum powder diluted in KBr powder. The lower spectrum was taken without the hemispherical attachment 14 of the invention present. The upper spectrum was taken under the same conditions with the attachment of the invention present. One can observe a 60–80% increase in throughput and a 20–30% increase in spectral contrast. Since the noise level is approximately the same for both spectra, the S/N ratio is also increased about 60–80%. The improvement in quality of the output with the invention will be plainly evident to those skilled in this art.

In a specific embodiment designed for use with the Praying Mantis Model accessory, the hemispherical body 14 had an inside diameter of about 25 mm, and was formed of aluminum or stainless steel with a polished mirrored interior to form the reflecting surface 15. The windows 16 and 17 were spaced openings cut into the body, positioned offset from the hemispherical peak and located on the side of the dome as illustrated in FIGS. 2 and 3, which views are approximately drawn to scale. The azimuth angle between the windows, designated 8 in FIG. 3, was approximately 120°, and each window was circular with a diameter of approximately 15 mm. Thus, the openings occupied approximately one-third of the dome surface area.

The location of the entrance window 16 allows the incident focussed beam 43 to impinge upon the sample at an angle of incidence that can be varied from between about 30° and 50°. While this is preferred for many sample materials, it is not intended to be limiting. Repositioning of the window 16 would allow different angles of incidence to be employed. The desirable range for most analyses is between 20° and 70°. Similarly, the exit window is symmetrically positioned on the same side of the dome at the indicated angle 8 so that specular reflections will not pass through but will be redirected by the reflecting dome back to the source or captured by the reflecting dome and reimaged back onto the sample.

In general, for best results, the geometry is chosen such that the solid angle defined by the center of curvature of the reflector 15 and the windows 16, 17, coincide with the solid angles defined by this same center and the surfaces of the focussing and collecting ellipsoids 30, 31. With this geometry, if one assumes completely random diffuse reflection, then the diffuse reflectance with the attachment of the invention present is given by:

$$R = Rt/(a + (1 - 2a) Rt),$$

where Rt is the total reflectance and a is the fraction of the diffusely reflected radiation that escapes through the windows 16 and 17.

The effect of the attachment is in general dependent upon the reflectivity of the sample. If reflectivity is low, there is little radiation that can be effectively used by the attachment of the invention. On the other hand, if reflectivity is high, the attachment will contribute significantly. This makes the attachment of the invention extremely useful in cases where a small amount of the sample is diluted in a non-absorbing (high reflecting) matrix and the presence of the sample can be noted by weak absorption peaks. In this case, the attachment will increase the spectral contrast amplifying those absorption peaks. An example of this is given in the graphs of FIG. 6.

The attachment of the invention can be used with accessories other than the Praying Mantis Model illustrated in FIG. 4, and will also be especially useful for the reasons given above for small samples, and due to the multiple reflections from the same sample point, which will enhance the S/N ratio and spectral contrast. As mentioned earlier, the attachment will also be of benefit with all spectrometers in the UV, VIS, and IR ranges which permit the use of diffuse reflectance accessories.

While the invention has been described in connection with a preferred embodiment and in specific applications by way of example, it will be understood by persons skilled in this art that the invention is not limited thereto but the principles thereof can be applied in various optical geometries and in many analytical applications, and the invention is to cover all modifications, equivalents and alternatives falling within the spirit and scope of the invention.

What is claimed is:

1. A method for improving the spectroanalysis of a sample of a material by diffuse reflectance spectrometry in a spectrometer providing a sampling compartment in the optical path of a radiation beam to a detector, comprising the steps:
   a. supporting the sample in a fixed position within the sampling compartment,
   b. redirecting the radiation beam so it is incident upon a surface of the sample at an angle between 20 and 70 degrees,
   c. providing a hollow body having an interior hemispherical reflecting surface and windows for entrance of a radiation beam and for allowing radiation to exit,
   d. surrounding the sample with the hemispherical reflecting surface in such a manner that the redirected incident beam will pass through the entrance window and impinge upon the sample and such that the center of curvature of the hemisphere substantially coincides with the impingement area on the sample of the incident beam,
   e. redirecting radiation exiting through the exit window of the hollow body toward the detector, and
   f. detecting the redirected radiation exiting from the body and using the detected radiation to determine a characteristic of the sample,
   g. said entrance and exit windows being spaced from one another, and the exit window being located in a position to allow predominantly diffusely reflected radiation from the sample to exit through it.

2. The method of claim 1 wherein the sample is provided with a reflecting medium.

3. A method as set forth in claim 1, wherein the sample is a diffuse reflector, the radiation is UV, VIS, or IR, and the incident radiation beam is focussed at substantially a point of the sample located substantially at the center of curvature of the hemispherical reflecting surface.

4. A method as set forth in claim 3 wherein the entrance and exit windows are offset at an angle of about 120° to prevent specular radiation from exiting.

5. An attachment for use with an accessory for carrying out diffuse reflectance spectroscopy in a spectrometer wherein the accessory provides first means for focussing an incident radiation beam received from the spectrometer onto the surface of a sample to be analyzed and supported by the accessory and second means for collecting diffused reflections from the sample surface and redirecting it back into the spectrometer for detection and processing of the resultant signal; the attachment comprising a hollow body having an interior hemispherical reflecting surface, an entrance window for receiving the incident beam and an exit window for allowing diffused reflections from the sample to exit from the body, the entrance and exit windows being spaced openings in the body located offset from the hemispherical peak, said attachment being positioned over the sample such that the area of impingement of the incident beam on the sample surface substantially coincides with the center of curvature of the interior reflecting surface.

6. An accessory for performing diffuse reflectance analysis of a sample in an UV, VIS, or IR spectrometer comprising:
   a. a base member configured to fit within the sampling compartment of the spectrometer,
   b. means on the base member for supporting a sample in a fixed position,
   c. optical means for receiving an incident radiation beam from the spectrometer and focussing the beam onto substantially an impingement point of the sample surface such that diffuse reflectance occurs producing diffuse reflectance rays carrying information about a characteristic of the sample in many directions,
   d. a removable body having an interior hemispherical reflecting surface provided over the sample such that the center of curvature of the reflecting surface substantially coincides with the impingement point on the sample of the incident beam, those reflected rays which are intercepted by the reflecting surface being reimaged at substantially the same impingement point,
   e. an entrance window in the body for allowing the incident beam to impinge upon the sample,
   f. an exit window in the body for allowing predominantly diffuse reflectance radiation to exit from the body,
   g. optical means on the base member for collecting radiation exiting from the body and redirecting same back into the spectrometer for detection and processing of the resultant signals therein.

7. An accessory as claimed in claim 6 wherein the entrance window is located on the body so as to allow the incident beam to impinge upon the sample at an angle of incidence between 20° and 70°, and the exit window is offset from the entrance window and is located so as to allow to exit diffused reflections, but not specular radiation, from the body at an angle of incidence between 20° and 70°.

8. An accessory as claimed in claim 7 wherein the entrance and exit windows occupy approximately one-thrid of the surface of the hemispherical reflector.

9. An accessory as claimed in claim 8 wherein the hemispherical surface has a diameter of about 25 mm, and the windows are circular openings each having a diameter of about 15 mm.

* * * * *